(12) United States Patent
Moore et al.

(10) Patent No.: US 11,807,614 B1
(45) Date of Patent: Nov. 7, 2023

(54) METHOD FOR MAKING SUBSTITUTED FURAN COMPOUND EMBODIMENTS AND DERIVATIVES THEREOF

(71) Applicant: Triad National Security, LLC, Los Alamos, NM (US)

(72) Inventors: Cameron Moore, White Rock, NM (US); Andrew Sutton, Oak Ridge, TN (US); Xiaokun Yang, Santa Fe, NM (US)

(73) Assignee: Triad National Security, LLC, Los Alamos, NM (US)

( * ) Notice: Subject to any disclaimer, the term of this patent is extended or adjusted under 35 U.S.C. 154(b) by 0 days.

(21) Appl. No.: 17/559,034

(22) Filed: Dec. 22, 2021

Related U.S. Application Data

(60) Provisional application No. 63/130,506, filed on Dec. 24, 2020.

(51) Int. Cl.
| | | |
|---|---|---|
| *C07D 307/36* | (2006.01) | |
| *B01J 27/053* | (2006.01) | |
| *B01J 21/18* | (2006.01) | |
| *B01J 23/44* | (2006.01) | |

(52) U.S. Cl.
CPC ............ *C07D 307/36* (2013.01); *B01J 21/18* (2013.01); *B01J 23/44* (2013.01); *B01J 27/053* (2013.01)

(58) Field of Classification Search
CPC .................................................. C07D 307/36
See application file for complete search history.

(56) References Cited

U.S. PATENT DOCUMENTS

| | | |
|---|---|---|
| 5,468,490 A | 11/1995 | Huber et al. |
| 5,627,288 A | 5/1997 | Fukawa et al. |
| 6,994,875 B2 | 2/2006 | Piccirilli et al. |
| 2014/0303114 A1 | 10/2014 | Mesina |

OTHER PUBLICATIONS

Milner et al., "Alkylation of furan catalysed by arenetricarbonylmolybdenum," *J. Organometallic Chemistry*, 217(2): 199-203, Sep. 8, 1981.
Nienhouse et al, "Convenient synthesis of substituted furans" *J. Am. Chem. Soc.*, 89(17): 4557-4558, Aug. 1, 1967.
Rodriguez-Saona et al., "Alkylfurans: Effects of Alkyl Side-Chain Length on Insecticidal Activity," *J. Nat. Prod.*, vol. 62, pp. 191-193, Nov. 20, 1998.
Rodriguez-Saona et al., "Novel antifeedant and insecticidal compounds from avocado idioblast cell oil," *Journal of Chemical Ecology*, 24(5): 867-889, May 1998.
Wailzer et al., "Structural Features for Furan-Derived Fruity and Meaty Aroma Impressions," *Natural Product Communications*, 11(10): 1475-1479, Oct. 1, 2016.
Weyerstahl et al., "Constituents of the leaf essential oil of *Persea indica* (L.) K. Spreng.," *Flavour and Fragrance Journal*, 8(4): 201-207, Jul./Aug. 1993.

*Primary Examiner* — Sikarl A Witherspoon
(74) *Attorney, Agent, or Firm* — Klarquist Sparkman, LLP

(57) ABSTRACT

Disclosed herein are embodiments of a method for making substituted furan compounds using bioderived coupling partners and a heterogeneous catalyst. In particular disclosed embodiments, the method comprises coupling a furan compound with the coupling partner (e.g., an aliphatic or heteroaliphatic coupling partner) in the presence of the heterogeneous catalyst to provide the substituted furan compound.

14 Claims, 13 Drawing Sheets

METHOD FOR MAKING SUBSTITUTED FURAN COMPOUND EMBODIMENTS AND DERIVATIVES THEREOF

CROSS REFERENCE TO RELATED APPLICATIONS

This application claims the benefit of and priority to the earlier filing date of U.S. Provisional Patent Application No. 63/130,506, filed Dec. 24, 2020, which is incorporated herein by reference in its entirety.

ACKNOWLEDGMENT OF GOVERNMENT SUPPORT

This invention was made with government support under Contract No. 89233218CNA000001 awarded by the U.S. Department of Energy/National Nuclear Security Administration. The government has certain rights in the invention.

FIELD

The present disclosure is directed to embodiments of a method for making substituted furan compound embodiments and derivatives thereof.

BACKGROUND

Naturally occurring alkyl furans have been used in numerous applications. Rose furan, which is isolated from Bulgarian rose oil, is an aroma compound used in fragrances. Other alkyl furans, such as 2-pentylfuran, are approved for use as food flavoring compounds. Alkyl furans isolated from avocado fruit have been demonstrated to have beneficial properties for skin health and also show promise as anti-inflammatory therapeutics. Hydrogenated versions of avocado furans are also promising naturally-derived insecticides for crop protection. While there are myriad applications for alkylated furans, methods for making such compounds are lacking. There exists a need in the art for a new and efficient method of making substituted furan compounds that does not require expensive catalysts and/or that avoids chemical waste.

SUMMARY

Disclosed herein are embodiments of a method, comprising reacting a first feedstock comprising a furan compound with a second feedstock comprising an coupling partner in the presence of a heterogeneous catalyst to provide a substituted furan have a structure according to Formula I

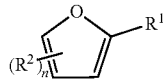

Formula I wherein $R^1$ is an aliphatic group or an aliphatic-aromatic group provided by the coupling partner; and when n is 1, then $R^2$ is methyl or is the same as $R^1$, and when n is 0, then $R^2$ is not present.

In some embodiments, the ratio of the first feedstock to the second feedstock ranges from 2:1 to 20:1.

In any or all of the above embodiments, the ratio of the first feedstock to the second feedstock ranges from 5:1 to 15:1.

In any or all of the above embodiments, the ratio of the first feedstock to the second feedstock ranges from 5:1 to 10:1.

In any or all of the above embodiments, n is 0.

In any or all of the above embodiments, n is 1 and $R^2$ is methyl.

In some embodiments, the ratio of the second feedstock to the first feedstock ranges from 2:1 to 5:1.

In any or all of the above embodiments, n is 1 and $R^2$ is the same as $R^1$.

In any or all of the above embodiments, the heterogeneous catalyst is present in an amount ranging from greater than 0 wt % to 50 wt % of the second feedstock.

In any or all of the above embodiments, the heterogeneous catalyst is present in an amount ranging from 10 wt % to 50 wt % of the second feedstock.

In any or all of the above embodiments, the furan compound is furan, 2-methyl furan, 3-methyl furan, or a combination thereof.

In any or all of the above embodiments, the coupling partner is a bioderived compound.

In any or all of the above embodiments, the coupling partner comprises an aliphatic group or an aliphatic-aromatic group that is coupled to a terminal hydroxyl group.

In any or all of the above embodiments, the coupling partner comprises an aliphatic group or an aliphatic-aromatic group that is coupled to a terminal conjugated diene moiety In any or all of the above embodiments, the coupling partner is selected from prenol, farnesol, geraniol, cinnamyl alcohol, phytol, myrcene, or any combination thereof.

In any or all of the above embodiments, the coupling partner comprises a heteroaliphatic group or a heteroaliphatic-aromatic group that is coupled to a terminal hydroxyl group.

In any or all of the above embodiments, the coupling partner comprises a heteroaliphatic group or a heteroaliphatic-aromatic group that is coupled to a terminal conjugated diene moiety In any or all of the above embodiments, the method further comprises converting the substituted furan to a hydrogenated product by exposing the substituted furan to a hydrogenation catalyst comprising palladium on a support material selected from activated carbon or $BaSO_4$ in the presence of $H_2$ gas.

Also disclosed herein are embodiments of a method, comprising: reacting a first feedstock comprising a furan compound with a second feedstock comprising a coupling partner in the presence of a heterogeneous catalyst to provide a substituted furan have a structure according to Formula I

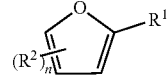

Formula I wherein $R^1$ is an aliphatic group or an aliphatic-aromatic group provided by the coupling partner; and when n is 1, then $R^2$ is methyl or is the same as $R^1$, and when n is 0, then $R^2$ is not present; and exposing the substituted furan to a hydrogenation catalyst comprising palladium on a support material selected from activated carbon or $BaSO_4$ in the presence of $H_2$ gas to provide a selectively hydrogenated substituted furan wherein no olefins of the furan ring are hydrogenated.

Also disclosed herein are embodiments of a method, comprising:

combining a first feedstock, a second feedstock, and a catalyst to provide a feedstock reaction mixture;

allowing the feedstock reaction mixture to mix for a time suitable to provide a substituted furan compound having a structure according to Formula I; and isolating the substituted furan compound, wherein Formula I is

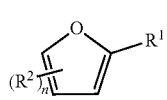

Formula I wherein $R^1$ is an aliphatic group or an aliphatic-aromatic group provided by the coupling partner; and when n is 1, then $R^2$ is methyl or is the same as $R^1$, and when n is 0, then $R^2$ is not present.

In some embodiments, the method further comprises exposing the substituted furan to a hydrogenation catalyst comprising palladium on a support material selected from activated carbon or $BaSO_4$ in the presence of $H_2$ gas to provide a selectively hydrogenated substituted furan, wherein no olefins of the furan ring are hydrogenated.

Also disclosed herein are compounds selected from 2-(3,7-dimethyloctyl)furan or 2-(3,7,11-trimethyl-2,6,10-dodecanyl)furan.

The foregoing and other objects and features of the present disclosure will become more apparent from the following detailed description, which proceeds with reference to the accompanying figures.

DETAILED DESCRIPTION

1. Overview of Terms

Figure 1A:
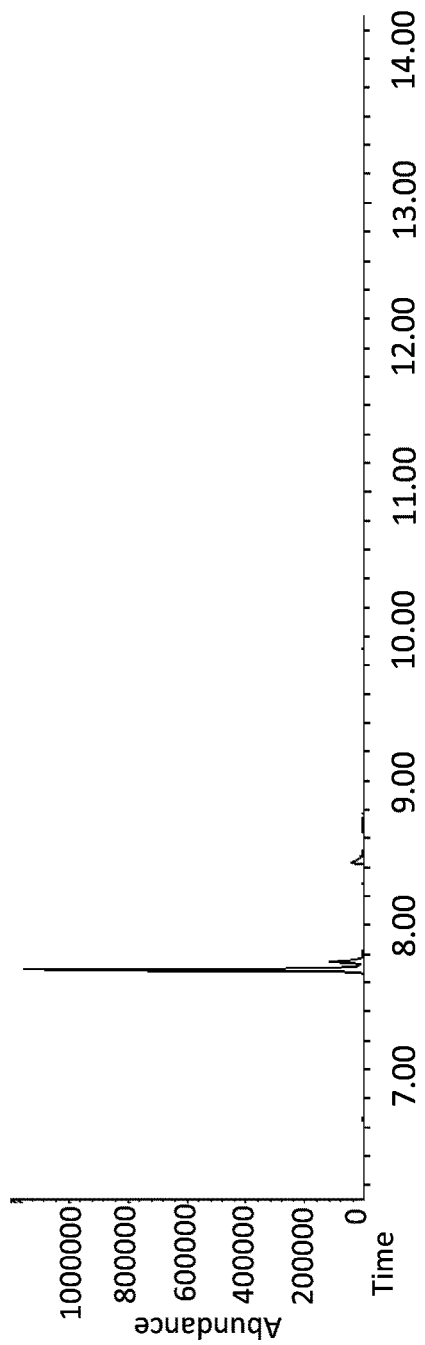
FIGS. 1A-1C show gas chromatograms (FIGS. 1A and 1B) and a mass spectrum (FIG. 1C) showing results of using a disclosed method embodiment to convert furan to 2-(3-methyl-2-buten-1-yl)furan, a representative substituted furan embodiment, using prenol as an aliphatic coupling partner.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Although the steps of disclosed method(s) are described in a particular, sequential order for convenient presentation, it should be understood that this manner of description encompasses rearrangement, unless a particular ordering is required by specific language set forth below. For example, steps described sequentially may in some cases be rearranged or performed concurrently. Additionally, the description sometimes uses terms like "produce" and "provide" to describe the disclosed methods. These terms are high-level abstractions of the actual steps that are performed. The actual steps that correspond to these terms will vary depending on the particular implementation and are readily discernible by one of ordinary skill in the art.

Unless explained otherwise, all technical and scientific terms used herein have the same meaning as commonly understood to one of ordinary skill in the art to which this disclosure belongs. Although methods and compounds similar or equivalent to those described herein can be used in the practice or testing of the present disclosure, suitable methods and compounds are described below. The compounds, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided. Certain functional group terms include a symbol "-" which is used to show how the defined functional group attaches to, or within, the compound to which it is bound. Also, a dashed bond (i.e., "- - -") as used in certain formulas described herein indicates an optional bond (that is, a bond that may or may not be present). A person of ordinary skill in the art would recognize that the definitions provided below and the compounds and formulas included herein are not intended to include impermissible substitution patterns (e.g., methyl substituted with 5 different groups, and the like). Such impermissible substitution patterns are easily recognized by a person of ordinary skill in the art. In formulas and compounds disclosed herein, a hydrogen atom is present and completes any formal valency requirements (but may not necessarily be illustrated) wherever a functional group or other atom is not illustrated. For example, a phenyl ring that is drawn as

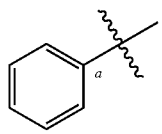 [SMILES: *c1ccccc1]

comprises a hydrogen atom attached to each carbon atom of the phenyl ring other than the "a" carbon, even though such hydrogen atoms are not illustrated. Any functional group disclosed herein and/or defined above can be substituted or unsubstituted, unless otherwise indicated herein.

Aliphatic: A hydrocarbon group having at least one carbon atom to 50 carbon atoms ($C_{1-50}$), such as one to 25 carbon atoms ($C_{1-25}$), or one to ten carbon atoms ($C_{1-10}$), and which includes alkanes (or alkyl), alkenes (or alkenyl), or alkynes (or alkynyl), including cyclic versions thereof, and further including straight- and branched-chain arrangements, and all stereo and positioned isomers as well. Aliphatic groups can further include substituted aliphatic groups, such as aliphatic groups comprising an aromatic substituent.

Aliphatic-Aromatic: A group comprising an aliphatic group coupled to an aromatic group and wherein the aliphatic-aromatic group is coupled to furan compound through the aliphatic group.

Aliphatic Coupling Partner: A compound comprising an aliphatic group and/or an aliphatic-aromatic group and that further comprises a terminal conjugated diene moiety and/or a terminal hydroxyl group. In some embodiments, the aliphatic coupling partner comprises a terminal conjugated diene moiety but no terminal hydroxyl group. In some embodiments, the aliphatic coupling partner comprises the terminal hydroxyl group, but no terminal conjugated diene moiety.

Alkenyl: An unsaturated monovalent hydrocarbon having at least two carbon atoms to 50 carbon atoms ($C_{2-50}$), such as two to 25 carbon atoms ($C_{2-25}$), or two to ten carbon atoms ($C_{2-10}$), and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cycloalkenyl), cis, or trans (e.g., E or Z).

Alkyl: A saturated monovalent hydrocarbon having at least one carbon atom to 50 carbon atoms ($C_{1-50}$), such as one to 25 carbon atoms ($C_{1-25}$), or one to ten carbon atoms ($C_{1-10}$), wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkynyl: An unsaturated monovalent hydrocarbon having at least two carbon atoms to 50 carbon atoms ($C_{2-50}$), such as two to 25 carbon atoms ($C_{2-25}$), or two to ten carbon atoms ($C_{2-10}$), and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Aromatic: A cyclic, conjugated group or moiety of, unless specified otherwise, from 5 to 15 ring atoms having a single ring (e.g., phenyl) or multiple condensed rings in which at least one ring is aromatic (e.g., naphthyl, indolyl, or pyrazolopyridinyl); that is, at least one ring, and optionally multiple condensed rings, have a continuous, delocalized π-electron system. Typically, the number of out of plane π-electrons corresponds to the Hückel rule (4n+2). The point of attachment to the parent structure or aliphatic group (such as in an aliphatic-aromatic group) typically is through an aromatic portion of the condensed ring system. For example,

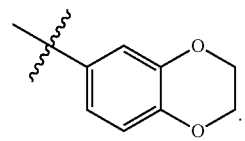 [SMILES: *c1ccc2c(c1)OCCO2]

However, in certain examples, context or express disclosure may indicate that the point of attachment is through a non-aromatic portion of the condensed ring system. For example,

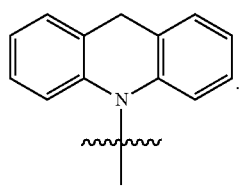 [SMILES: *N1c2ccccc2Cc2ccccc21]

An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si), such as in a heteroaryl group or moiety. Aromatic groups may be substituted with one or more groups other than hydrogen.

Aryl: An aromatic carbocyclic group comprising at least five carbon atoms to 15 carbon atoms ($C_{5-15}$), such as five to ten carbon atoms ($C_{5-10}$), having a single ring or multiple condensed rings, which condensed rings can or may not be aromatic. Aryl groups may be substituted with one or more groups other than hydrogen.

Biodrived Compound: An organic compound that is obtained from a natural source. Coupling partners (e.g., aliphatic and/or heteroaliphatic coupling partner) comprising terminal hydroxyl and/or conjugated diene functional groups can be bioderived compounds. In some embodiments, the furan compound can be a bioderived compound.

Furan Compound: An organic compound selected from furan or an alkylated furan (e.g., a methylated furan, such as 2-methyl furan or 3-methyl furan).

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, silicon, boron, selenium, phosphorous, and oxidized forms thereof within the group. Alkoxy, ether, amino, disulfide, peroxy, and thioether groups are exemplary (but non-limiting) examples of heteroaliphatic.

Heteroaliphatic-aromatic: A group comprising a heteroaliphatic group coupled to an aromatic group and wherein the heteroaliphatic-aromatic group is coupled to furan compound through the heteroaliphatic group.

Heteroaliphatic Coupling Partner: A compound comprising a heteroaliphatic group and/or a heteroaliphatic-aromatic group and that further comprises a terminal conjugated diene moiety and/or a terminal hydroxyl group. In some embodiments, the heteroaliphatic coupling partner comprises a terminal conjugated diene moiety but no terminal hydroxyl group. In some embodiments, the heteroaliphatic coupling partner comprises the terminal hydroxyl group, but no terminal conjugated diene moiety.

Heterogeneous Catalyst: A catalyst that exists in a phase different from the first feedstock, the second feedstock, or both the first and second feedstocks. In particular embodiments, the heterogeneous catalyst is a solid.

Hydrogenated Product: A compound that has one or more fewer degrees of unsaturation as compared to the substituted furan compound from which it is obtained. A selectively hydrogenated product is one wherein the furan ring is not hydrogenated.

Hydrogenation Catalyst: A catalyst or catalyst system that is capable of catalyzing a chemical reaction between molecular hydrogen ($H_2$) and one or more olefins of the aliphatic portion of a substituted furan compound provided by the coupling partner. In some embodiments, a hydrogenation catalyst comprises a metal and a support material.

Support Material: A material that supports a hydrogenation catalyst (or a metal thereof) to increase the surface area of the catalyst and/or improve its activity.

Terminal Conjugated Diene Moiety: A functional group of a coupling partner that has a formula $CH_2=CH-CH=CH_2-R$, wherein R comprises the aliphatic or heteroaliphatic (and/or aliphatic-aromatic and/or heteroaliphatic-aromatic) portion of the coupling partner.

Terminal Hydroxyl Group: A functional group of a coupling partner that has a formula —OH and that is bound to an $sp^3$ hybridized carbon atom of the coupling partner through the oxygen atom.

II. Introduction

Furan alkylation is conventionally accomplished using stoichiometric reagents, which are either difficult to prepare, proceed in low yield or create substantial amounts of chemical waste. Additionally, conventional methods for furan alkylation to produce fragrances, such as rose furan, involve using alkyl lithium reagents that must be handled under inert atmospheres at low temperatures and provide overall yields well below 50%. Alkyl lithium reagents are reactive and can be difficult to handle and often require increased safety procedures during use. The reactivity of the lithium reagents in such methods also results in undesired side reactions and thus can limit the feedstocks used in such methods.

Disclosed herein are method embodiments for making substituted furan compounds that address and/or avoid drawbacks associated with conventional methods, such as those discussed above. In some embodiments, the disclosed method embodiments produce less waste. In yet some additional embodiments, the disclosed method embodiments can be performed at ambient conditions without introducing additional chemical hazards (e.g., alkyl lithium reagents). In yet additional embodiments, the disclosed method embodiments proceed in high chemical yield. In particular embodiments, renewable reagents can be used in the method, and myriad products for myriad different industries can be made using method embodiments disclosed herein.

III. Method Embodiments

Disclosed herein are method embodiments for making a substituted furan compound and/or derivatives thereof. In particular embodiments, the substituted furan compound embodiments are furan compounds that comprise at least one substituent (e.g., an aliphatic, heteroaliphatic, aromatic, aliphatic-aromatic, or heteroaliphatic-aromatic substituent) that is introduced onto the furan compound skeleton by way of coupling the furan compound with a coupling partner (e.g., an aliphatic coupling partner or a heteroaliphatic coupling partner). In particular embodiments, the substituted furan compound has a structure according to Formula I, wherein $R^1$ is the substituent provided by the coupling partner. With reference to Formula I, n is 0 or 1 and thus $R^2$ can be present or not. In particular embodiments, the substituted furan compound does not comprise the illustrated $R^2$ (such as when n=0). In an independent embodiment, the $R^2$ group can be methyl (or another substituent) and can be present because the furan compound used as the first feedstock is a methylated furan (e.g., 2-methyl furan or 3-methyl furan). In yet another independent embodiment, the $R^2$ group can present because it results from reaction between a first feedstock comprising furan and second feedstock comprising a coupling partner in an amount sufficient to result in substituting the furan twice, thereby substituted the furan with $R^1$ and $R^2$ substituents.

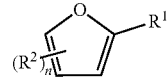

Formula I

In some embodiments, the substituted furan compound can have a structure according to any one of Formulas IA-ID.

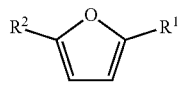

Formula IA

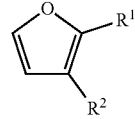

Formula IB

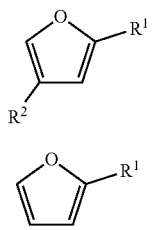

Formula IC

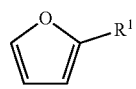

Formula ID

In particular embodiments of any of Formulas I or IA-ID, $R^1$ can be an aliphatic group, such as an alkyl group or an alkenyl group; an aliphatic-aromatic group, such as an alkyl-aryl or alkenyl-aryl group; a heteroaliphatic group, such as a heteroalkyl or heteroalkenyl group; or a heteroaliphatic-aromatic group, such as heteroalkyl-aryl or heteroalkenyl-aryl; and $R^2$ can be methyl or a group as defined for $R^1$.

In particular embodiments, the method comprises reacting a first feedstock and a second feedstock in the presence of a heterogeneous catalyst to provide a substituted furan having a structure according to Formula I. In some embodiments, the method comprises combining the first feedstock, the second feedstock, and the heterogeneous catalyst to provide a feedstock reaction mixture; allowing the feedstock reaction mixture to mix for a time and at a temperature suitable to provide a substituted furan compound; and isolating the substituted furan compound. In particular embodiments, the first feedstock comprises a furan compound and the second feedstock comprises a coupling partner, such as an aliphatic coupling partner or a heteroaliphatic coupling partner.

The first feedstock comprises a furan compound. In particular embodiments, the first feedstock comprises furan, 2-methyl furan, 3-methyl furan, or any combination thereof. In exemplary embodiments, the first feedstock comprises furan. In particular embodiments, the first feedstock comprises a neat solution of the furan compound wherein no solvent is included with the furan compound. In other embodiments, the furan compound can be combined with a solvent. In some embodiments, the first feedstock can be provided as a continuous feed or as a batch-wise feed.

The second feedstock comprises a coupling partner, such as an aliphatic coupling partner or a heteroaliphatic coupling partner. In particular embodiments, the coupling partner is a bioderived compound obtainable from renewable processes. In some embodiments, the coupling partner can be a terpene, such as a hemiterpene, a monoterpene, a sesquiterpene, and the like. In particular embodiments, the coupling partner can be an aliphatic coupling partner that comprises an aliphatic group comprises a terminal hydroxyl group and/or a conjugated diene motif; or an aliphatic-aromatic group that comprises a terminal hydroxyl group and/or a conjugated diene motif. In yet other embodiments, the coupling partner can be a heteroaliphatic coupling partner that comprises a heteroaliphatic group comprises a terminal hydroxyl group and/or a conjugated diene motif; or a heteroaliphatic-aromatic group that comprises a terminal hydroxyl group and/or a conjugated diene motif. In particular embodiments, the coupling partner comprises an aliphatic group (or an aliphatic-aromatic group) or a heteroaliphatic group (or a heteroaliphatic-aromatic group) comprising a terminal hydroxyl group and/or a conjugated diene motif that is covalently coupled to an aliphatic or heteroaliphatic group having from 1 to 50 carbon atoms, such as 1 to 20 carbon atoms, or 1 to 5 carbon atoms. In some embodiments, the aliphatic group (or the aliphatic portion of the aliphatic-aromatic group) is an alkenyl group comprising one to 3 double bonds, such as one to 2 double bonds, or one double bonds. Exemplary coupling partners comprising a terminal alcohol can include, but are not limited to, prenol, farnesol, geraniol, cinnamyl alcohol, phytol, or combinations thereof. Exemplary coupling partners comprising a conjugated diene motif can include, but are not limited to, myrcene or other similar compounds. In some embodiments, the second feedstock is provided as a neat solution of the coupling partner, such that no solvent is used. In other embodiments, a solvent can be combined with the coupling partner. In some embodiments, the furan compound can further serve as a solvent. In some embodiments, the second feedstock can be provided as a continuous feed or as a batch-wise feed.

The heterogeneous catalyst can be a solid acid catalyst. In some embodiments, the heterogeneous catalyst is a protic acid catalyst, such as a Bronsted acid-based catalyst; or an ion exchange resin, such as a cation exchange resin. In particular embodiments, the heterogeneous catalyst can be a solid acid catalyst, such as a zeolite catalyst; or a polystyrene-based ion exchange resin. Exemplary heterogeneous catalysts can include, but are not limited to, Amberlyst 15 (a brown-grey solid and a macro reticular polystyrene based ion exchange resin with strongly acidic sulfonic group) or Nafion™ NR50 (a perfluorosulfonic acid Nafion resin) (both obtained from Sigma Aldrich); Perlkat® 79-3 or Perlkat® 46-10 (bead-shaped, amorphous silica gel with high alumina content solid) (obtained from BASF); an HZSM catalyst (e.g., HZSM-5, where Si:Al=15, 40, 145; such catalysts typically comprise several pentasil units [8 five-membered rings] linked together by oxygen bridges to form pentasil chains), or an HSY® catalyst, such as HSY® (Si:Al=2.55, 15) (characterized by large, essentially spherical, internal cavities linked tetrahedrally through pore openings of 0.8 nm and typically defined by rings of twelve oxygen atoms) (obtained from Zeolyst). In an independent embodiment, the heterogeneous catalyst can be a phosphate catalyst, such as $NbPO_4$. In particular embodiments, the heterogeneous catalyst is a zeolite catalyst, such as an aluminosilicate material having a silica-to-alumina ratio ranging from 2 to 280, such as 2 to 140, or 2 to 15.

In particular embodiments, the first feedstock, the second feedstock, and/or the heterogeneous catalyst can be combined in any order. In some embodiments, the method can comprise adding the second feedstock to the first feedstock, or adding the first feedstock to the second feedstock to provide a feedstock mixture and then combining the resulting feedstock mixture with the heterogeneous catalyst to provide a feedstock reaction mixture. In yet additional embodiments, the heterogeneous catalyst can first be combined with one of the first or second feedstocks and then the remaining feedstock can be added to provide the feedstock reaction mixture. In yet additional embodiments, the each of the first feedstock, the second feedstock, and the heterogeneous catalyst can be added simultaneously to a reaction vessel to provide the feedstock reaction mixture.

In some embodiments, the first feedstock and the second feedstock are provided at a particular ratio relative to one another. In some embodiments, the first feedstock and second feedstock are used at a ratio ranging from 2:1 to 20:1 (first feedstock:second feedstock), such as 5:1 to 15:1 or 5:1 to 10:1. In particular embodiments, the ratio is 2:1, 5:1, 7.5:1, 8:1, or 10:1 (first feedstock:second feedstock). In some embodiments, it can be desired to obtain a substituted furan compound that comprises two aliphatic and/or aliphatic-aromatic substituents (e.g., such as illustrated in Formulas IA, IB, or IC). In such embodiments, the method can comprise using an excess of the second feedstock relative to the first feedstock. For example, in such embodiments, the second feedstock and first feedstock are used at a ratio ranging from 2:1 to 20:1 (second feedstock:first feedstock). The catalyst can be used in an amount ranging from greater than 0 wt % to 50 wt % with respect to the amount of the second feedstock, such as 5 wt % to 50 wt %, or 10 wt % to 50 wt %, or 10 wt % to 40 wt %, or 15 wt % to 30 wt % relative to the second feedstock. In particular embodiments, the catalyst was used in an amount ranging from 10 wt % to 50 wt % relative to the second feedstock.

The feedstock reaction mixture comprising the first feedstock, the second feedstock, and the catalyst can be allowed to mix for a time sufficient to provide the substituted furan. In some embodiments, the method can also comprise maintaining the feedstock reaction mixture at a particular temperature sufficient to ensure that none of the first or second feedstocks is volatilized. In some embodiments, the feedstock reaction mixture is allowed to mix at ambient temperature for a time period ranging from 2 minutes to 5 days, such as from 5 minutes to 96 hours, or 10 minutes to 72 hours, or 20 minutes to 60 hours, or 30 minutes to 24 hours. In particular embodiments, the reaction was allowed to mix at ambient temperature for 5 minutes, 10 minutes, 20 minutes, 30 minutes, 1.5 hours, 2 hours, 3 hours, 4 hours, 5 hours, 14 hours, 16 hours, 17 hours, 18 hours, 24 hours, 54 hours, 60 hours, 72 hours, 71 hours, and 96 hours. In some embodiments, the temperature can be reduced below ambient temperature. The feedstock reaction mixture can be allowed to mix in any suitable reaction vessel sufficient to contain the mixture. The progress of the reaction that provides the substituted furan can be monitored by evaluating the feedstock reaction mixture for the presence of the coupling partner. For example, thin layer chromatography and/or gas chromatography can be used to determine reaction progress.

In some embodiments, the method can further comprise performing one or more chemical transformations on the substituted furan compound to provide a derivative thereof. In some embodiments, the substituted furan compound can be hydrogenated and in particular embodiments can be selectively hydrogenated. In embodiments where the substituted furan compound is selectively hydrogenated, one or more sites of unsaturation on the appended coupling partner can be hydrogenated in the presence of the olefins of the furan ring. In other words, the olefins of the furan ring are not hydrogenated. In some embodiments, subsequent hydrogenation of the substituted furan compound can comprise exposing the substituted furan compound to palladium on a support material, such as activated carbon or BaSO$_4$, in a solvent, such as an alcohol solvent (e.g., methanol), and in the presence of H$_2$ gas. In some such embodiments, the method can be conducted at ambient temperature or at a temperature above ambient temperature (e.g., 40° C.). In some embodiments, selective hydrogenation is obtained along with full conversion of the substituted furan compound to the hydrogenated product. In some embodiments, novel products like 2-(3,7-dimethyloctyl)furan or 2-(3,7,11-trimethyl-2,6,10-dodecanyl)furan can be made using a hydrogenation method according to the present disclosure.

In yet additional embodiments, the method can further comprise performing further chemical reactions that further substituted the substituted furan compound. For example, in some embodiments, the substituted furan compound can be functionalized with a hydroxyl group, a halogen, an epoxide, and other substitutions that can occur at sites of unsaturation on the appended coupling partner and/or the furan ring. In particular embodiments, the substituted furan compound can be further functionalized with a sulfonate moiety (e.g., —SO$_3$Na or other sulfonate salt) by combining the substituted furan compound with sulfur trioxide, pyridine, and a sulfonating agent in a solvent (e.g., acetonitrile) and heating above ambient temperature (e.g., 40° C.). In some such embodiments, the sulfonate moiety can be added to the furan ring.

IV. Examples

As a representative example, the first feedstock, second feedstock, and the catalyst are added to a reaction vessel fitted with a magnetic stir bar. The resulting feedstock reaction mixture is stirred at room temperature for a suitable amount of time. The feedstock reaction mixture is then filtered to remove the solid catalyst using a filter Pasteur pipet or Buchner funnel. The filtered solution is then concentrated on a rotary evaporator to remove excess furan. Isolated yields are calculated by weight. Collected samples are diluted using ethyl acetate for GC-MS analysis, and using CDCl$_3$ for NMR analysis. Specific examples are provided herein.

GC-MS analysis was carried out using a Hewlett-Packard 7890 GC system equipped with a Hewlett-Packard 5973 mass selective detector, a Polyarc and an FID detector. $^1$H and $^{13}$C NMR spectra were obtained at room temperature on a Bruker AV400 MHz spectrometer, with chemical shifts (S) referenced to CDCl$_3$ signal ($^1$H and $^{13}$C).

Example 1

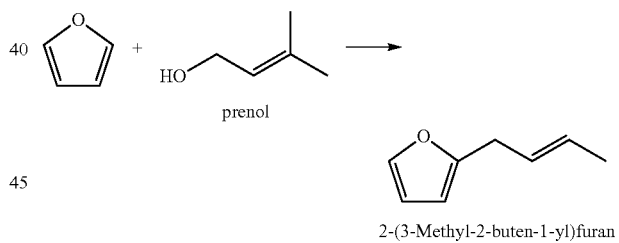

2-(3-Methyl-2-buten-1-yl)furan

Figure 1B:
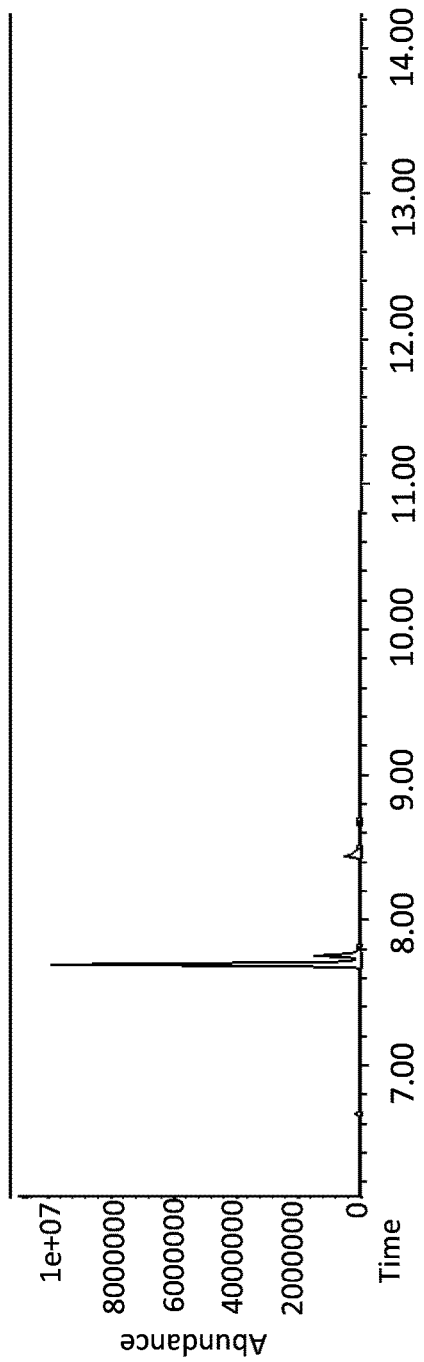
Figure 1C:
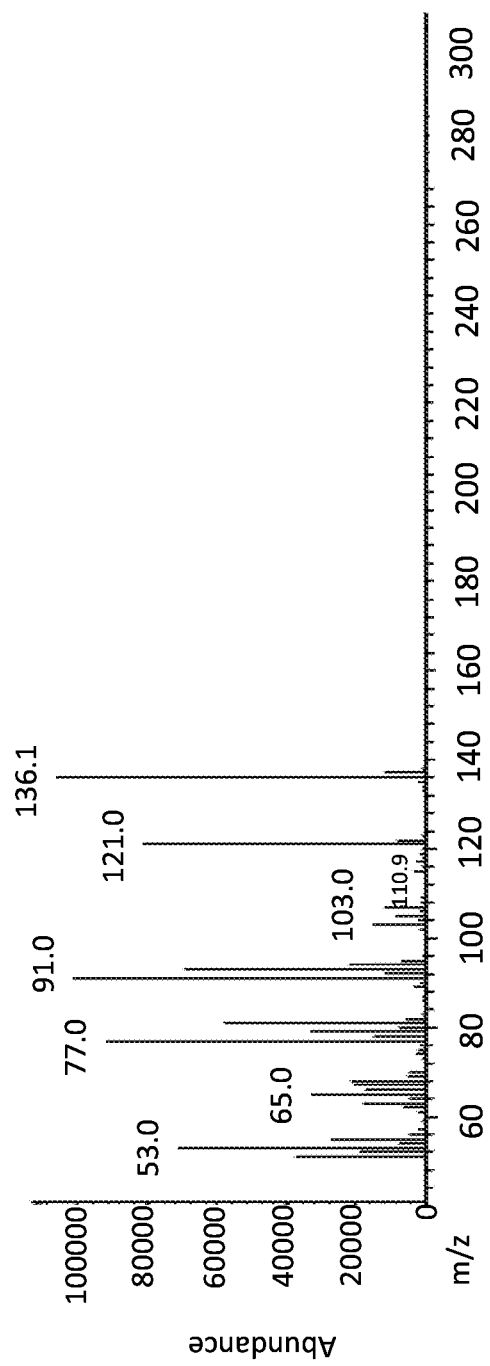
Figure 2A:
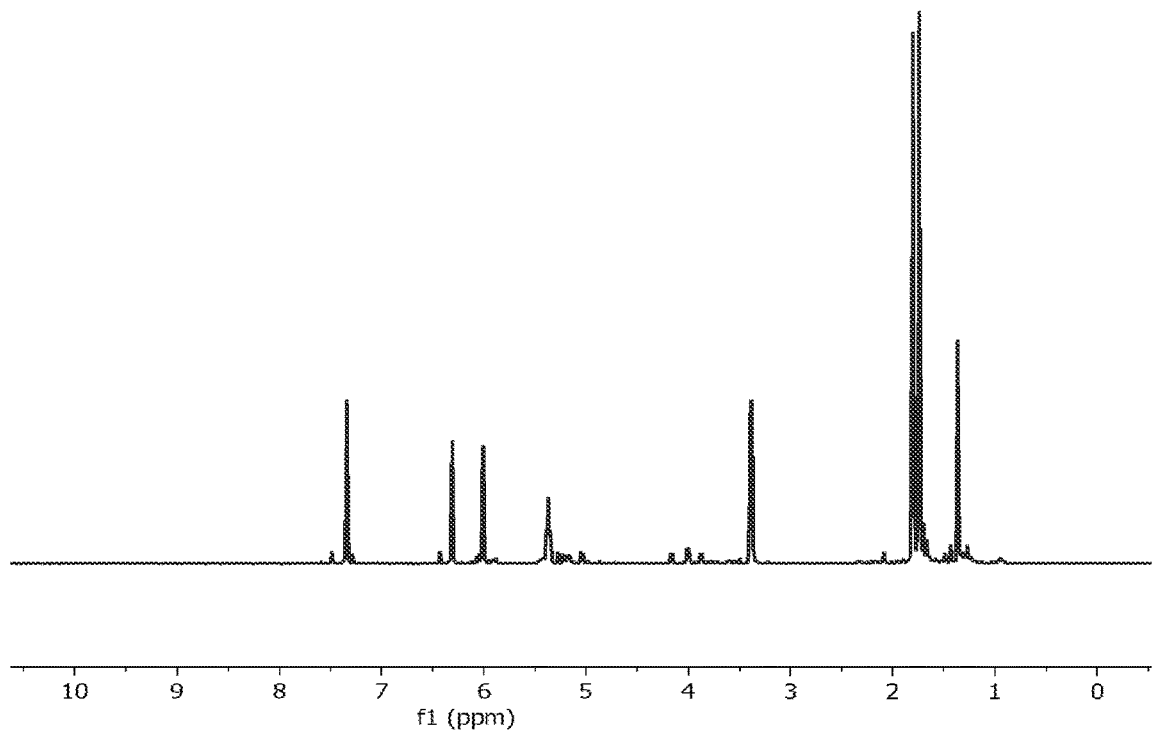
FIGS. 2A and 2B are $^1H$ NMR (FIG. 2A) and $^{13}C$ NMR (FIG. 2B) spectra of the substituted furan compound embodiment, 2-(3-methyl-2-buten-1-yl)furan.
Figure 2B:
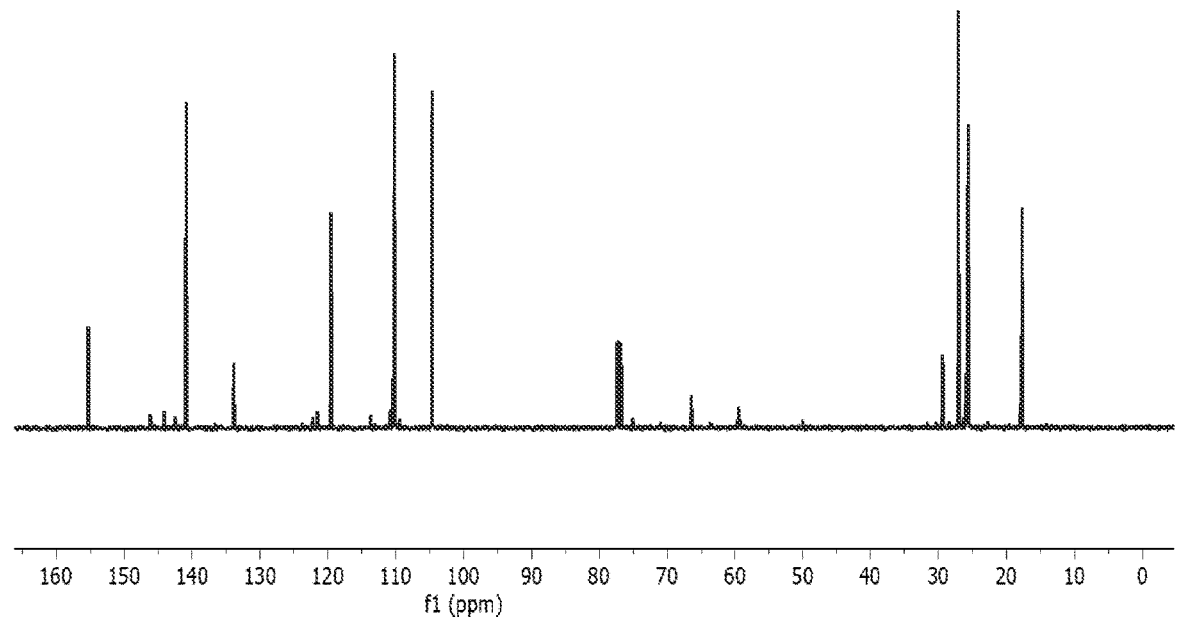
Figure 3A:
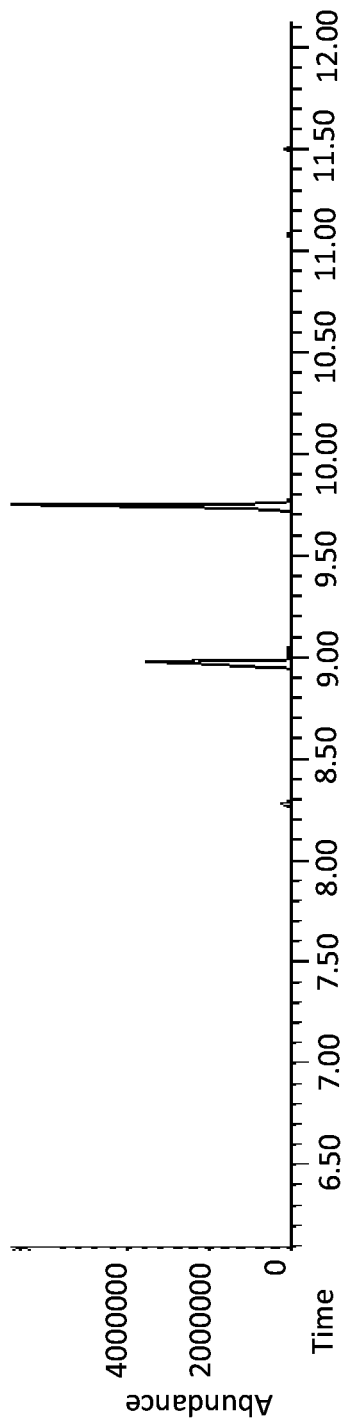
FIGS. 3A-3E show gas chromatograms (FIGS. 3A-3D) and a mass spectrum (FIG. 3E) showing the progress at different reaction times of a disclosed method embodiment to convert furan to 2-(3,7-dimethyl-2,6-octadien-1-yl)furan, a representative substituted furan embodiment using geraniol to as an aliphatic coupling partner.
Figure 3B:
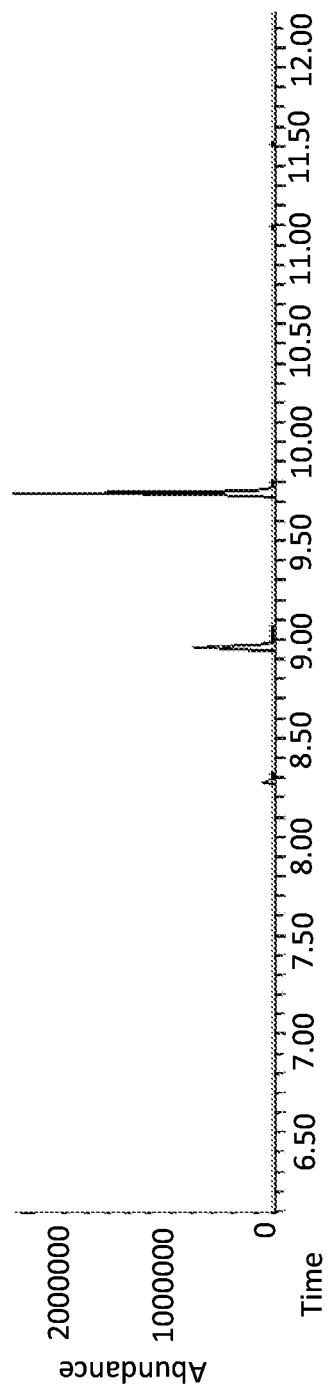
Figure 3C:
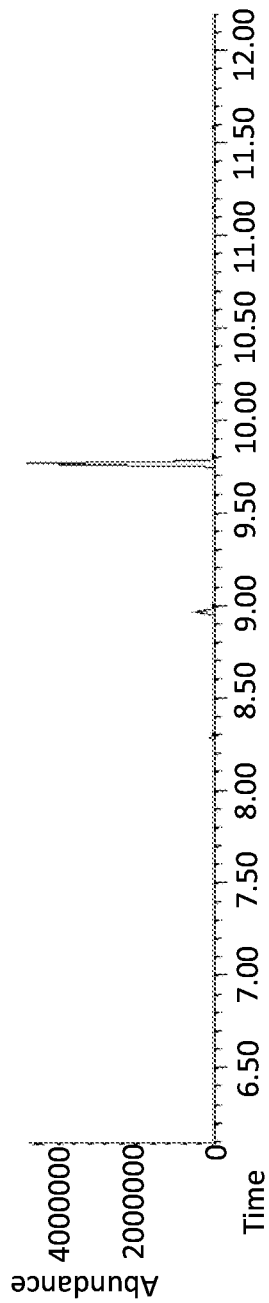
Figure 3D:
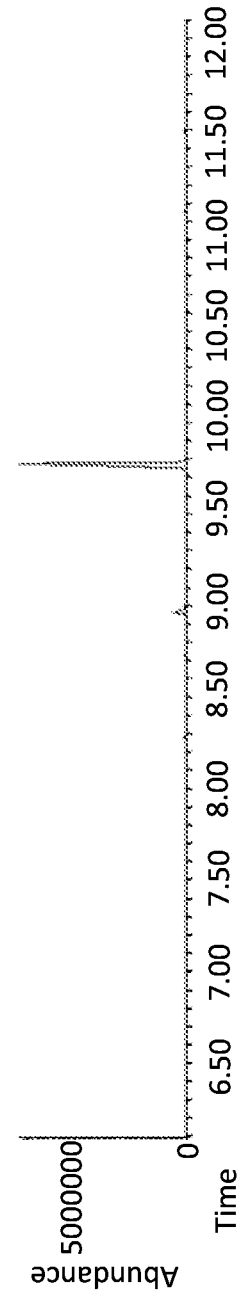
Figure 3E:
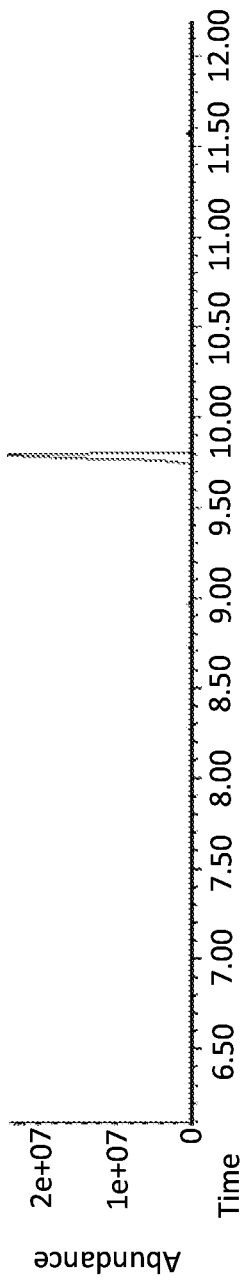

In this example, furan, prenol, and Amberlyst-15 were combined in a reaction vessel fitted with a magnetic stir bar. The resulting mixture was stirred at room temperature for 3 hours. The catalyst was removed by filtering and the filtered solution was concentrated on a rotary evaporator to remove excess furan. The selectively substituted furan product 2-(3-methyl-2-buten-1-yl)furan was obtained as evidenced by the GC spectra shown by FIGS. 1A-1C. $^1$H NMR (400 MHz, Chloroform-d) δ 7.34 (d, J=1.8 Hz, 2H), 6.31 (dd, J=3.2, 1.9 Hz, 2H), 6.01 (d, J=3.1 Hz, 2H), 5.37 (q, J=1.3 Hz, 1H), 3.39 (d, J=7.2 Hz, 4H), 1.80 (s, 7H); see FIG. 2A. $^{13}$C NMR (101 MHz, Chloroform-d) δ 155.35, 140.97, 133.95, 119.57, 110.21, 104.71, 27.16, 17.75; see FIG. 2B.

Additional examples using furan as a first feedstock and prenol as a second feedstock with various catalyst compounds (and/or catalyst amounts) are summarized in Table 1.

TABLE 1

| First Feedstock | Second Feedstock | Catalyst | Time (hours) | Selective conversion |
|---|---|---|---|---|
| Furan, 40 g | Prenol, 5 g | HSY (Si/Al = 15), 2.5 g | 2, 5, 24 | No |
| Furan, 5 g | Prenol, 0.5 g | Amberlyst-15, 0.05 g | 16 | Yes |
| Furan, 30 g | Prenol, 3 g | Amberlyst-15, 0.5 g | 3 | Yes |

Example 2

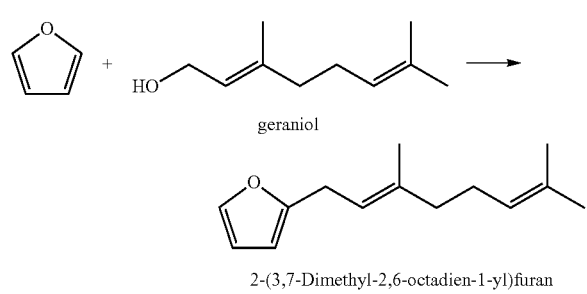

2-(3,7-Dimethyl-2,6-octadien-1-yl)furan

Figure 4A:
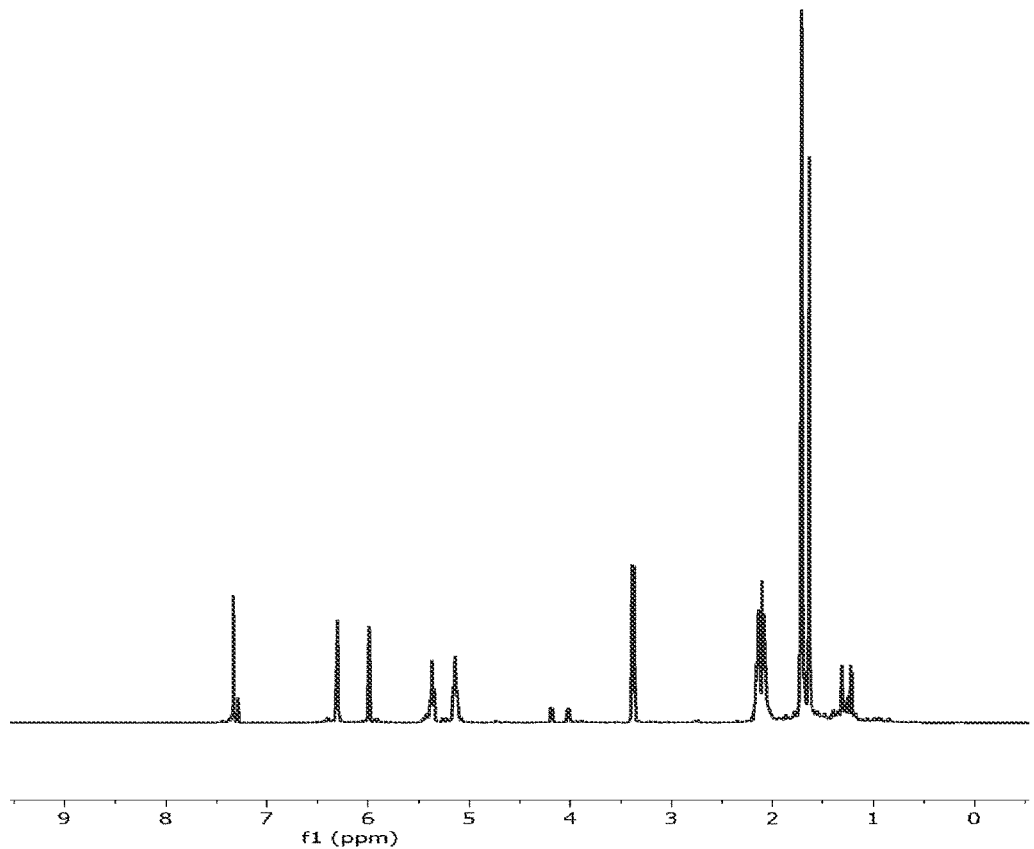
FIGS. 4A and 4B are $^1H$ NMR (FIG. 4A) and $^{13}C$ NMR (FIG. 4B) spectra of the substituted furan compound embodiment, 2-(3,7-dimethyl-2,6-octadien-1-yl)furan.
Figure 4B:
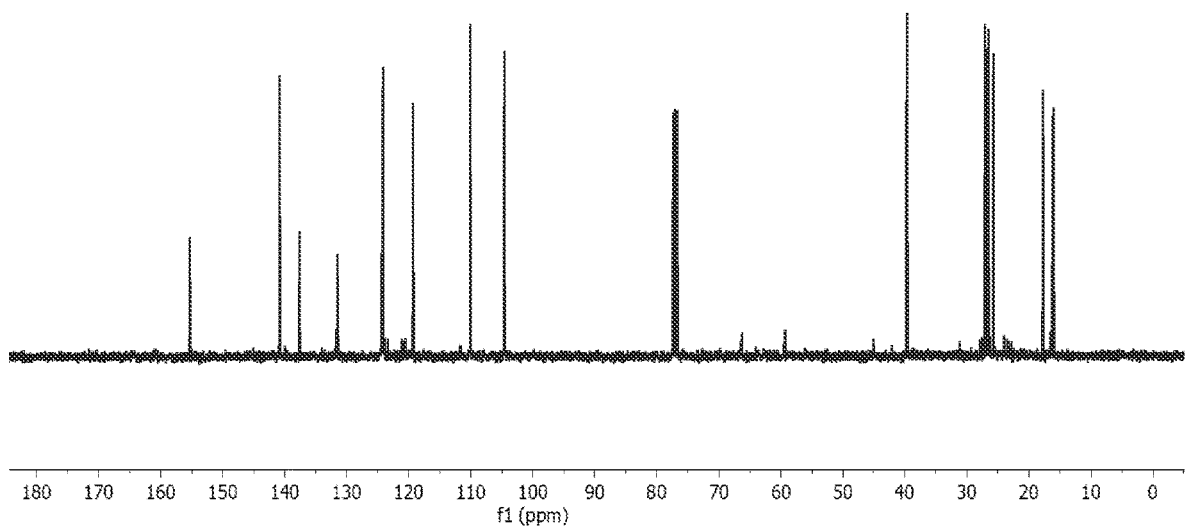

In this example, furan, geraniol, and HSY® (Si/Al=15) were combined in a reaction vessel fitted with a magnetic stir bar. The resulting mixture was stirred at room temperature for 3 hours. The catalyst was removed by filtering and the filtered solution was concentrated on a rotary evaporator to remove excess furan. The selectively substituted furan product 2-(3,7-dimethyl-2,6-octadien-1-yl)furan was obtained as evidenced by the GC spectra shown by FIGS. 3A-3E. $^1$H NMR (400 MHz, Chloroform-d) δ 7.33 (d, J=1.8 Hz, 1H), 6.30 (dd, J=3.2, 1.9 Hz, 1H), 5.99 (d, J=3.1 Hz, 1H), 5.37 (ddt, J=8.6, 7.3, 1.4 Hz, 1H), 5.14 (tq, J=4.7, 1.7 Hz, 1H), 3.38 (d, J=7.2 Hz, 1H), 2.23-2.03 (m, 4H), 1.79-1.54 (m, 9H); see FIG. 4A. $^{13}$C NMR (101 MHz, CDCl$_3$) δ 155.45, 141.01, 137.68, 131.61, 124.28, 119.39, 110.24, 104.76, 39.71, 27.11, 26.66, 25.81, 17.79, 16.17; see FIG. 4B Additional examples using furan as a first feedstock and geraniol as a second feedstock with various catalyst compounds (and/or catalyst amounts) are summarized in Table 2.

Example 3

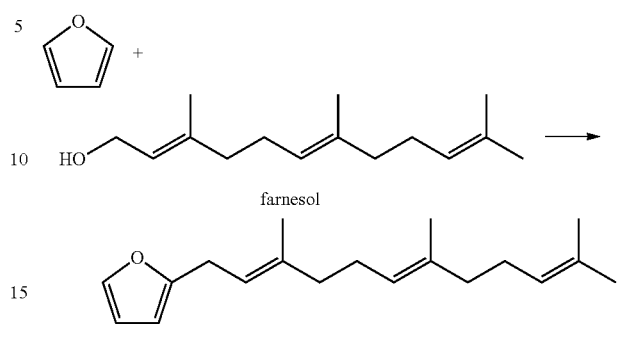

farnesol 2-(3,7,11)-Trimethyl-2,6,10-dodecatrien-1-yl)furan

Figure 5A:
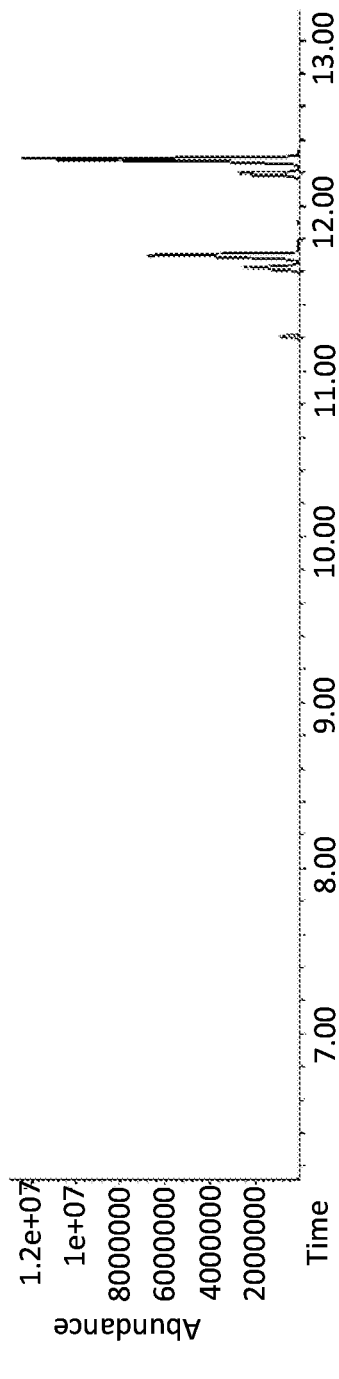
FIGS. 5A-5C show gas chromatograms (FIGS. 5A and 5B) and a mass spectrum (FIG. 5C) showing results of a disclosed method embodiment to convert furan to 2-(3,7,11-trimethyl-2,6,10-dodecatrien-1-yl)furan, a representative substituted furan embodiment, using farnesol as an aliphatic coupling partner.
Figure 5B:
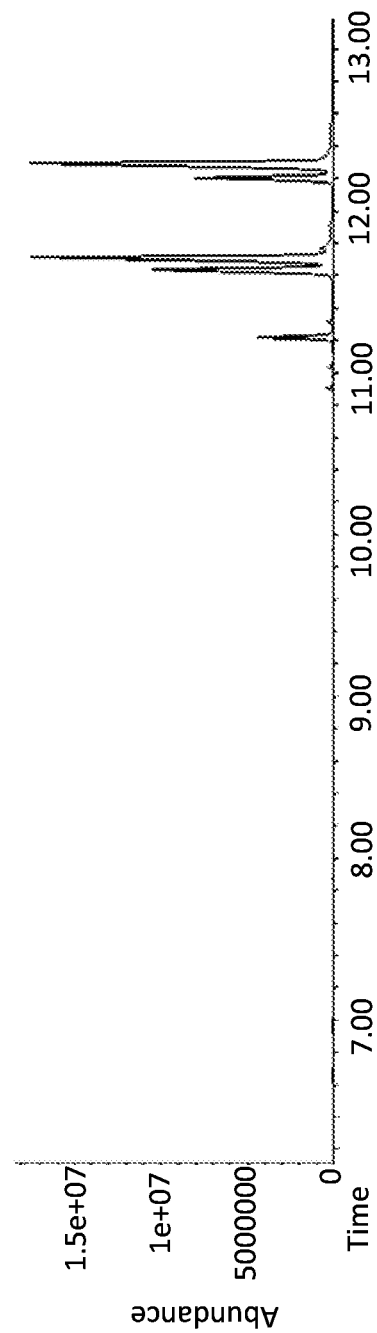
Figure 5C:
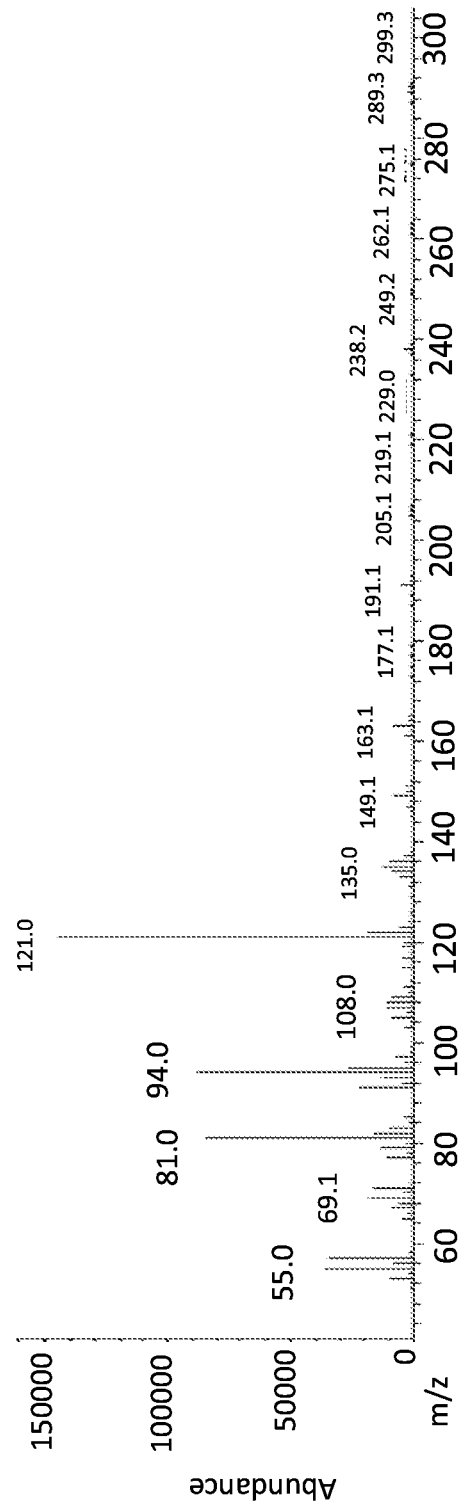
Figure 6A:
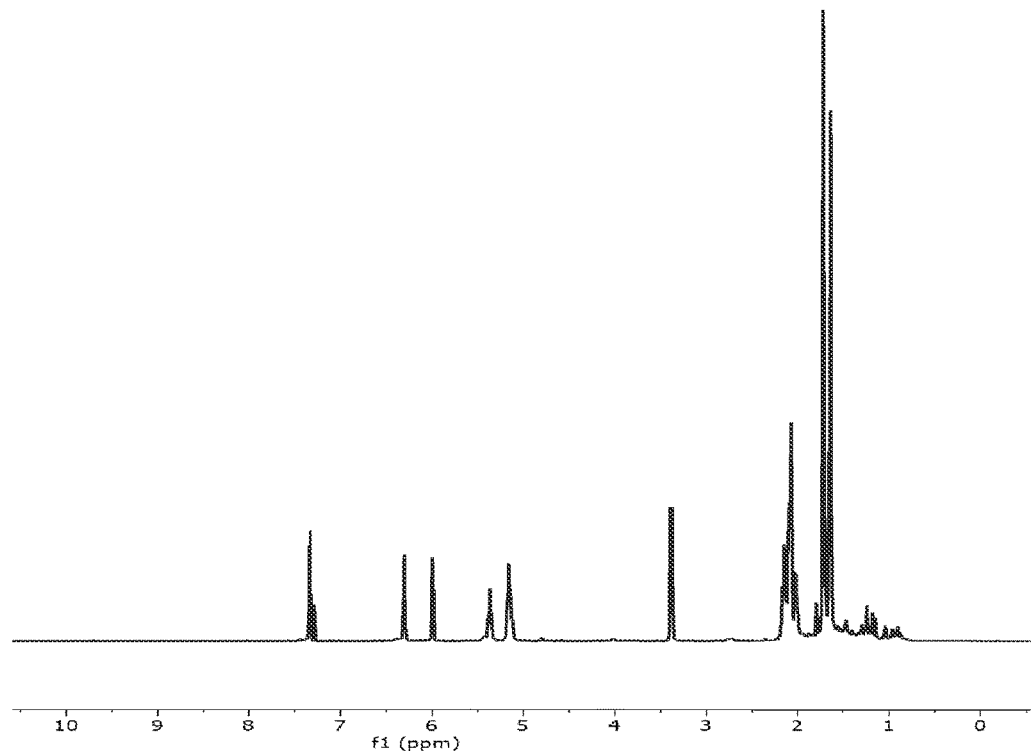
FIGS. 6A and 6B are $^1H$ NMR (FIG. 6A) and $^{13}C$ NMR (FIG. 6B) spectra of the substituted furan compound embodiment, 2-(3,7,11-trimethyl-2,6,10-dodecatrien-1-yl)furan.
Figure 6B:
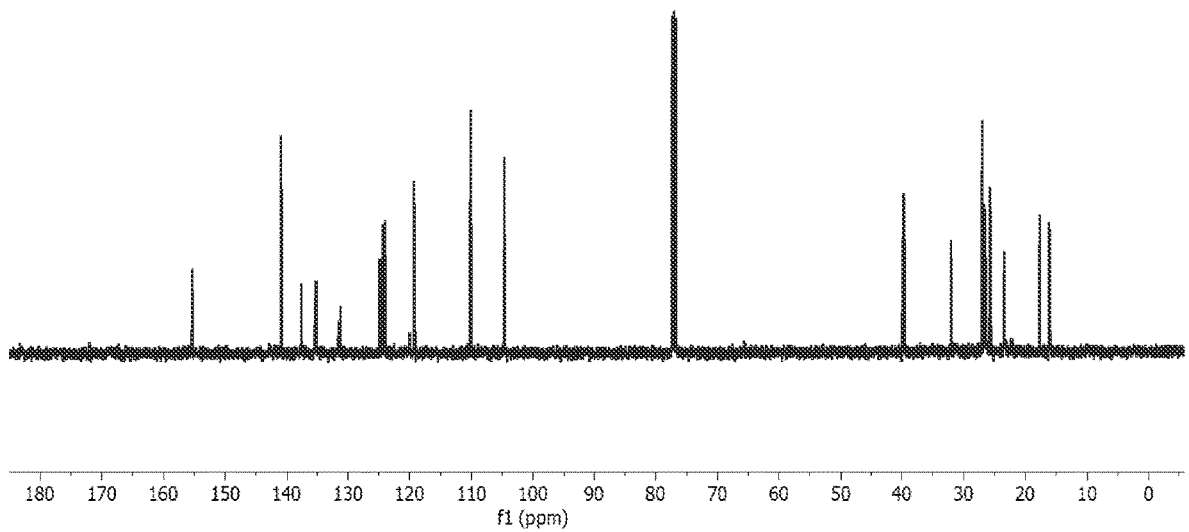

In this example, furan, farnesol, and Amberlyst-15 were combined in a reaction vessel fitted with a magnetic stir bar. The resulting mixture was stirred at room temperature for 3 hours. The catalyst was removed by filtering and the filtered solution was concentrated on a rotary evaporator to remove excess furan. The selectively substituted furan product 2-(3,7,11-trimethyl-2,6,10-dodecatrien-1-yl)furan was obtained as evidenced by the GC spectra shown by FIGS. 5A-5C. $^1$H NMR (400 MHz, Chloroform-d) δ 7.49-7.21 (m, 1H), 6.30 (dt, J=3.2, 1.7 Hz, 1H), 5.99 (d, J=3.2 Hz, 1H), 5.37 (t, J=7.3 Hz, 1H), 5.14 (dt, J=11.6, 6.8 Hz, 2H), 3.38 (d, J=7.1 Hz, 2H), 2.25-1.95 (m, 9H), 1.89-1.56 (m, 14H); see FIG. 6A. $^{13}$C NMR (101 MHz, CDCl$_3$) δ 155.46, 141.03, 137.73, 135.29, 131.39, 124.98, 124.52, 119.40, 110.26, 104.79, 39.86, 27.13, 26.87, 25.85, 17.81, 16.23; see FIG. 6B.

Example 4

In this example, furan (1.4 g), farnesol (0.6 g), and a HSY® (Si/Al=15) catalyst (0.3 g) were combined in a reaction vessel fitted with a magnetic stir bar. The resulting mixture was stirred at room temperature for 3 hours. The catalyst was removed by filtering and the filtered solution was concentrated on a rotary evaporator to remove excess furan. The selectively substituted furan product 2-(3,7,11-trimethyl-2,6,10-dodecatrien-1-yl)furan was obtained.

TABLE 2

| First Feedstock | Second Feedstock | Catalyst | Time | Selective conversion |
|---|---|---|---|---|
| Furan, 5 g | Geraniol, 0.5 g | Amberlyst-15, 0.05 g | 5, 10, 20, 60 mins, 4 hours | No |
| Furan, 5 g | Geraniol, 0.5 g | NbPO$_4$, 0.5 g | 5, 10 min, 2, 17 hours | No |
| Furan, 30 g | Geraniol, 3.5 g | HSY (Si/Al = 15), 1.7 g | 14 | Yes |
| Furan, 80 g | Geraniol, 10 g | HSY (Si/Al = 15), (1 + 2) = 3 g | 81 h | Yes |
| Furan, 80 g | Geraniol, 10 g | HSY (Si/Al = 15), 3 g | 60 h | Yes |
| Furan, 80 g | Geraniol, 10 g | HSY (Si/Al = 15), (3 + 1 + 1) = 5 g | 96 h | Yes |
| Furan, 80 g | Geraniol, 10 g | HSY (Si/Al = 15), (3 + 1) = 4 g | 72 h | Yes |
| Furan, 80 g | Geraniol, 10 g | HSY (Si/Al = 15), (3 + 1) = 4 g | 72 h | Yes |
| Furan, 150 g | Geraniol, 20 g | HSY (Si/Al = 15), (5 + 1 + 1 + 1) = 8 g | 54 h | Yes |

Example 5

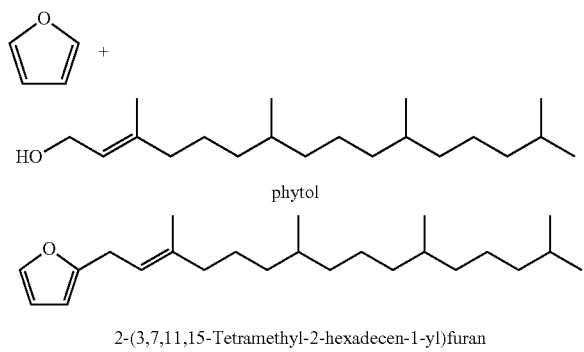

phytol 2-(3,7,11,15-Tetramethyl-2-hexadecen-1-yl)furan

Figure 7A:
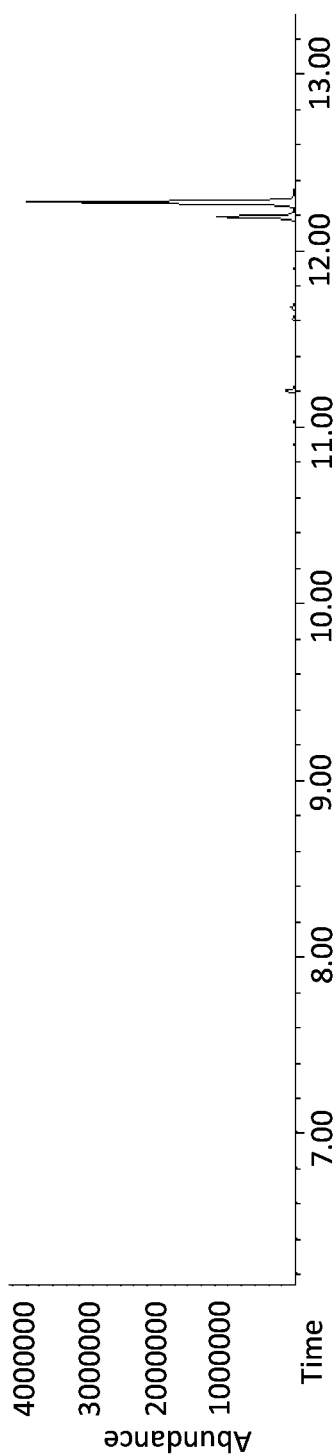
FIGS. 7A-7B show a gas chromatogram (FIG. 7A) and a mass spectrum (FIG. 7B) showing results of a disclosed method embodiment to convert furan to 2-(3,7,11,15-tetramethyl-2-hexadecen-1-yl)furan, a representative substituted furan embodiment, using phytol as an aliphatic coupling partner.
Figure 7B:
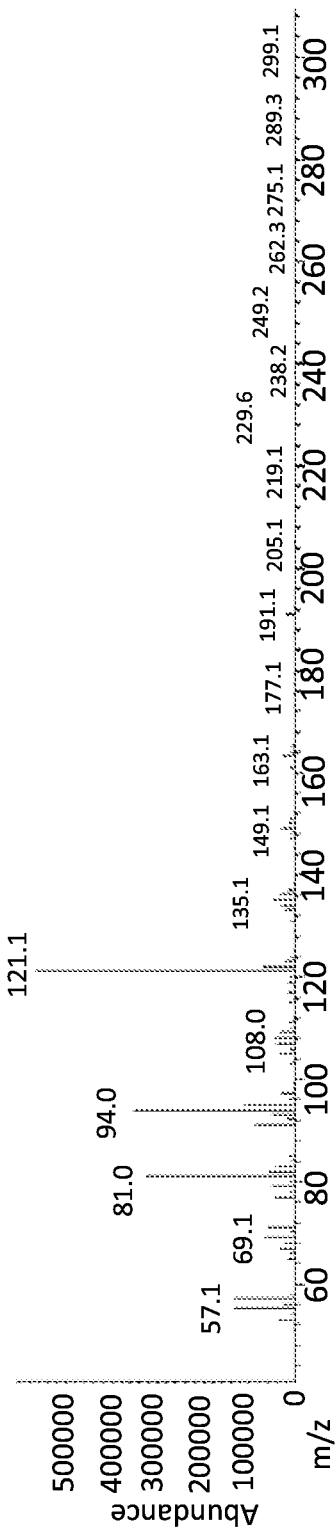
Figure 8A:
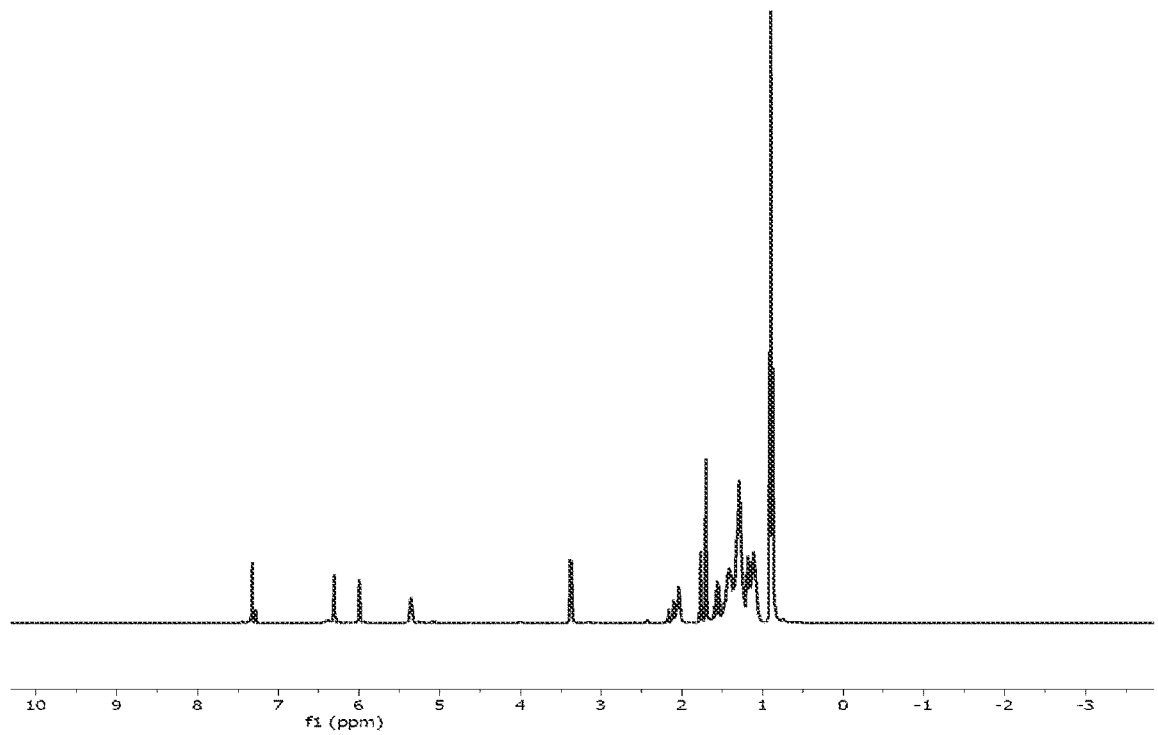
FIGS. 8A and 8B are $^1H$ NMR (FIG. 8A) and $^{13}C$ NMR (FIG. 8B) spectra of the substituted furan compound embodiment, 2-(3,7,11,15-tetramethyl-2-hexadecen-1-yl)furan).
Figure 8B:
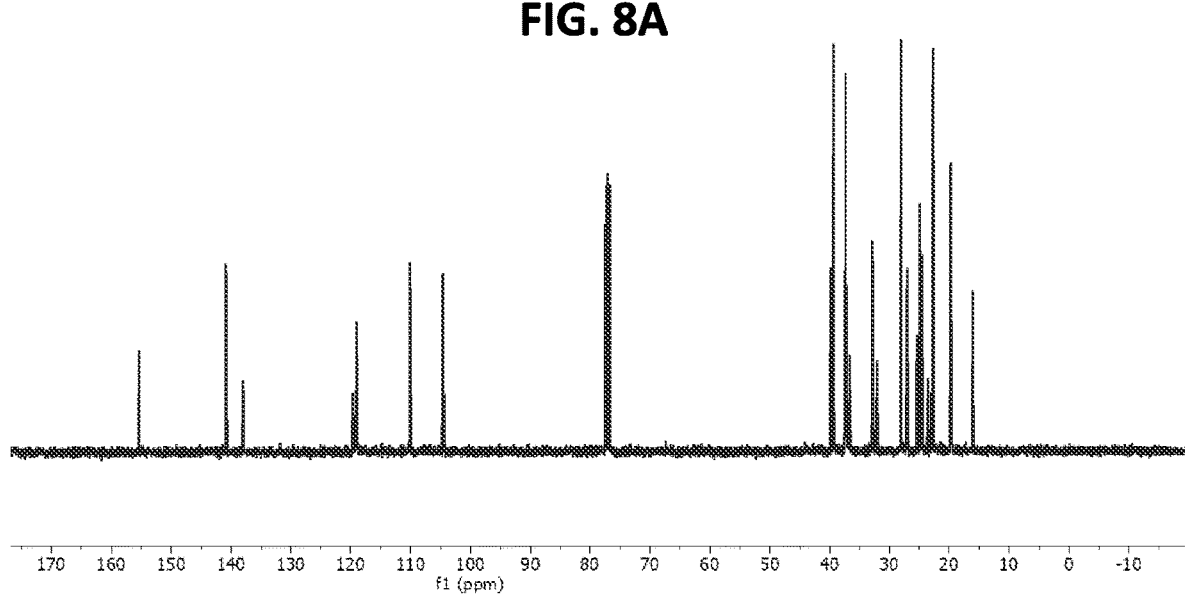

In this example, furan, phytol, and HSY® (Si/Al=15) catalyst were combined in a reaction vessel fitted with a magnetic stir bar. The resulting mixture was stirred at room temperature for 3 hours. The catalyst was removed by filtering and the filtered solution was concentrated on a rotary evaporator to remove excess furan. The selectively substituted furan product 2-(3,7,11,15-tetramethyl-2-hexadecen-1-yl)furan was obtained as evidenced by the GC spectra shown by FIGS. 7A and 7B. $^1$H NMR (400 MHz, Chloroform-d) δ 7.43-7.24 (m, 1H), 6.30 (dd, J=3.3, 1.8 Hz, 1H), 6.00 (d, J=3.1 Hz, 1H), 5.36 (t, J=7.5 Hz, 1H), 3.38 (d, J=7.1 Hz, 2H), 2.25-1.98 (m, 2H), 1.80-1.68 (m, 3H), 1.56 (dp, J=13.4, 6.7 Hz, 2H), 1.49-1.22 (m, 1 OH), 1.22-1.04 (m, 7H), 0.90 (dd, J=8.8, 6.6 Hz, 17H); see FIG. 8A. $^{13}$C NMR (101 MHz, CDCl$_3$) δ 155.54, 141.01, 138.13, 119.14, 110.28, 104.80, 40.05, 39.53, 37.60, 37.55, 37.46, 36.88, 32.95, 32.23, 28.13, 27.14, 25.42, 24.97, 24.63, 22.87, 22.78, 19.90, 19.84, 16.15; see FIG. 8B.

Example 6

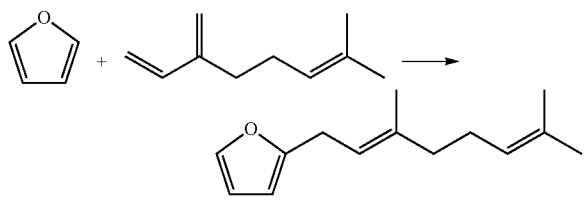

Figure 9A:
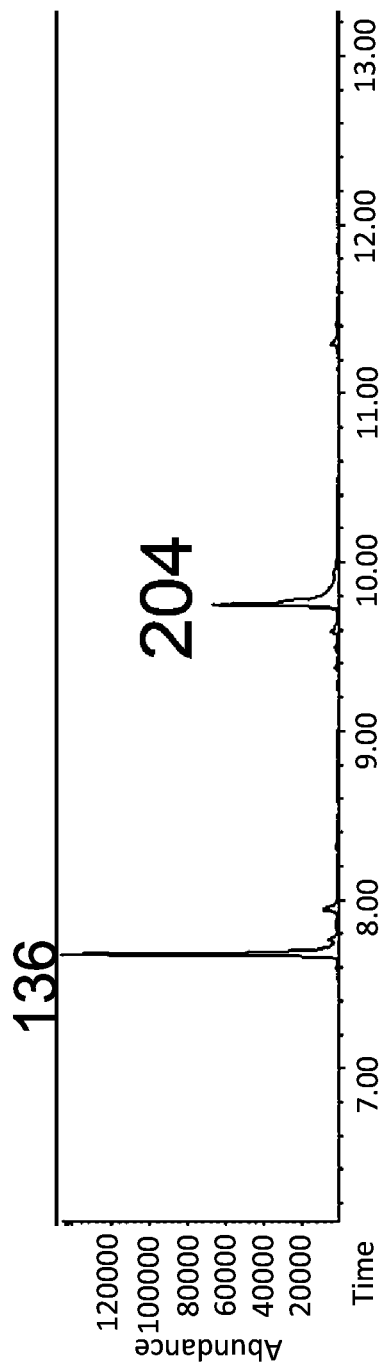
FIGS. 9A-9B show a gas chromatogram (FIG. 9A) and a mass spectrum (FIG. 9B) showing results of a disclosed method embodiment to convert furan to 2-(3,7-dimethyl-octa-2,6-dien-1-yl)furan, a representative substituted furan embodiment, using myrcene as an aliphatic coupling partner.
Figure 9B:
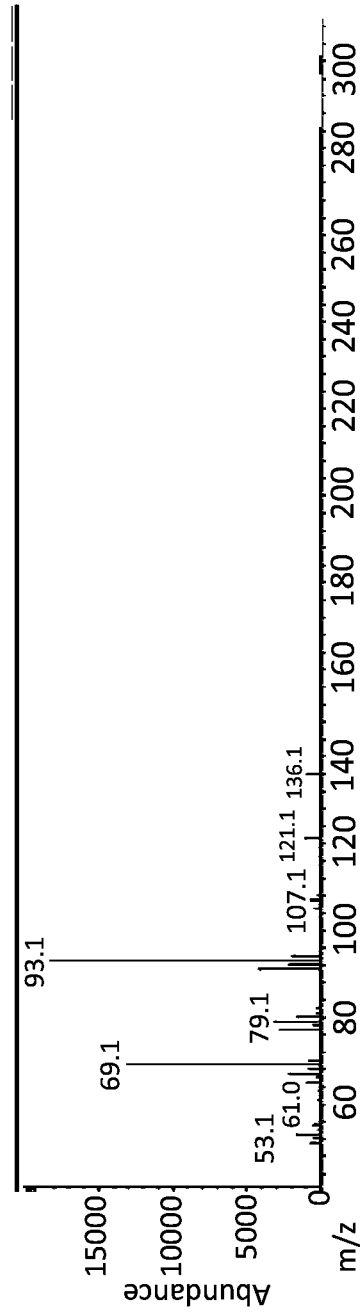

In this example, furan, myrcene, and HSY® (Si/Al=15) catalyst were combined in a reaction vessel fitted with a magnetic stir bar. The resulting mixture was stirred at room temperature for 24 hours. The catalyst was removed by filtering and the filtered solution was concentrated on a rotary evaporator to remove excess furan. The selectively substituted furan product 2-(3,7-dimethyl-2,6-octadien-1-yl)furan was obtained as evidenced by the GC spectra shown by FIGS. 9A and 9B.

Example 7

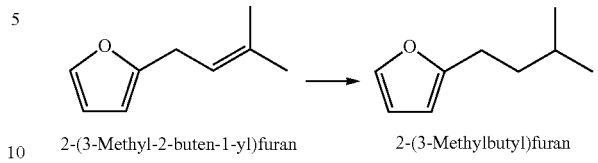

2-(3-Methyl-2-buten-1-yl)furan    2-(3-Methylbutyl)furan

In this example, 2-(3-methyl-2-buten-1-yl)furan, methanol, and Pd/C (en) catalyst were combined in a reaction vessel fitted with a magnetic stir bar. Hydrogen balloon was used as hydrogen source during the reaction. The resulting mixture was stirred at room temperature for 3 hours. The catalyst was removed by filtering and the filtered solution was concentrated on a rotary evaporator to remove solvent. The selectively substituted furan product 2-(3-methylbutyl)furan was obtained.

Example 8

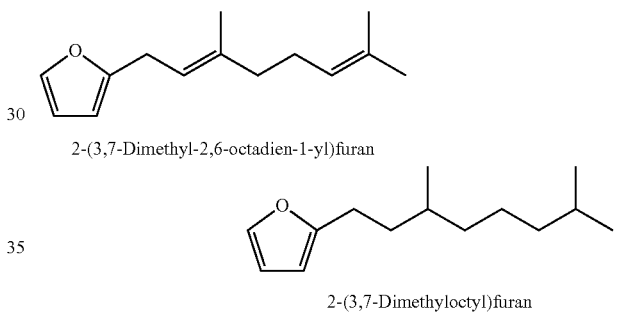

2-(3,7-Dimethyl-2,6-octadien-1-yl)furan 2-(3,7-Dimethyloctyl)furan

Figure 10A:
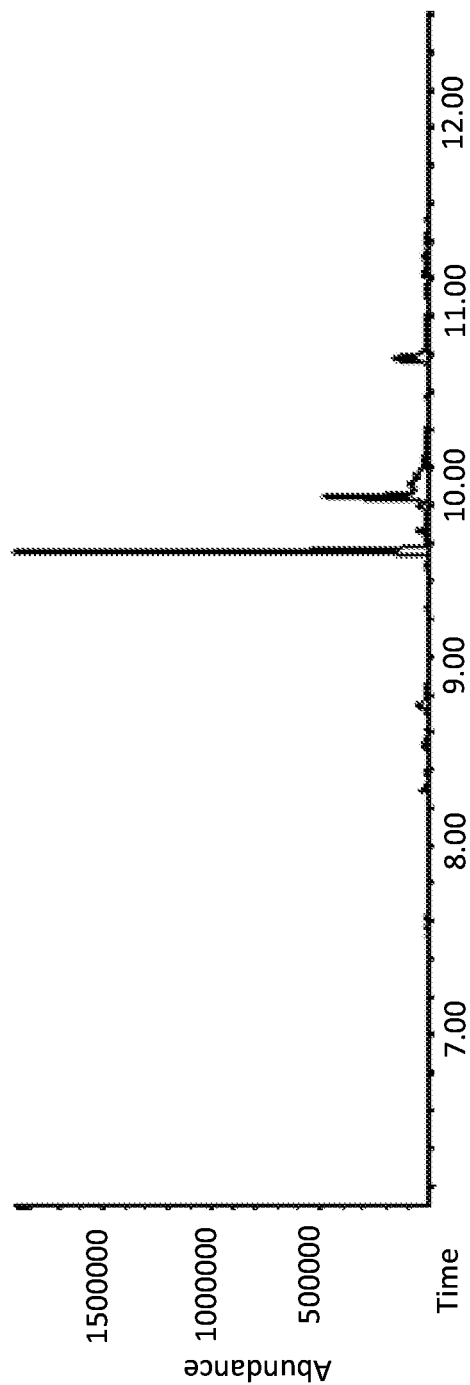
FIGS. 10A-10B show a gas chromatogram (FIG. 10A) and a mass spectrum (FIG. 10B) showing results of a reaction wherein a substituted furan compound embodiment is selectively hydrogenated to provide a hydrogenated derivative.
Figure 10B:
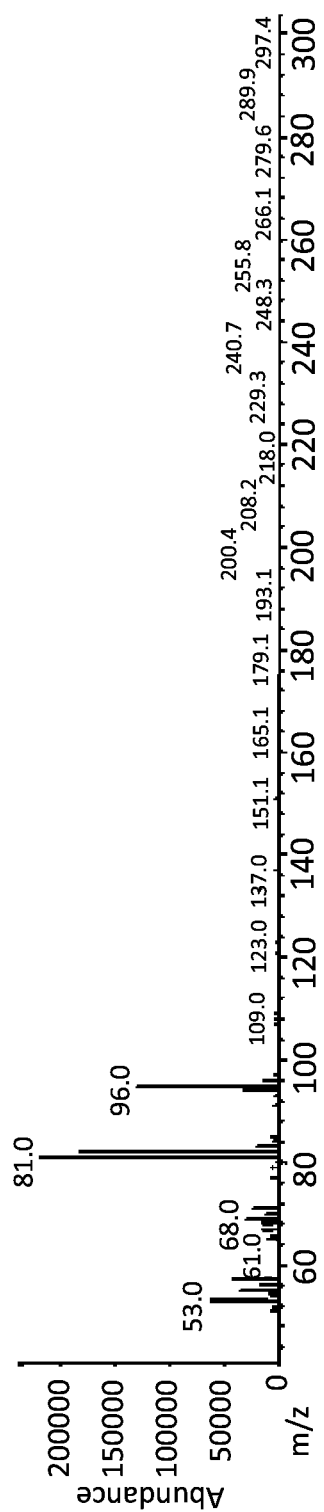

In this example, 2-(3,7-Dimethyl-2,6-octadien-1-yl)furan, methanol and Pd/C (en) catalyst were combined in a stainless steel reaction vessel fitted with a magnetic stir bar. 100 psi hydrogen gas was charged at room temperature. The resulting mixture was stirred at 40° C. for 3 hours. The catalyst was removed by filtering and the filtered solution was concentrated on a rotary evaporator to remove solvent. The selectively substituted furan product 2-(3,7-Dimethyloctyl)furan was obtained as evidenced by the GC spectra shown by FIGS. 10A and 10B.

Example 9

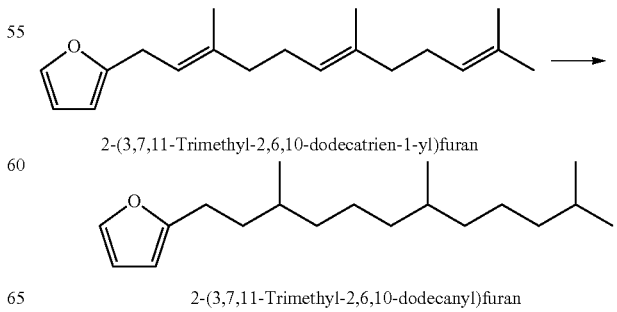

2-(3,7,11-Trimethyl-2,6,10-dodecatrien-1-yl)furan 2-(3,7,11-Trimethyl-2,6,10-dodecanyl)furan In this example, 2-(3,7,11-Trimethyl-2,6,10-dodecatrien-1-yl)furan, methanol and Pd/C (en) catalyst were combined in a stainless steel reaction vessel fitted with a magnetic stir bar. Hydrogen balloon was used as hydrogen source during the reaction. The resulting mixture was stirred at room temperature for 3 hours. The catalyst was removed by filtering and the filtered solution was concentrated on a rotary evaporator to remove solvent. The selectively substituted furan product 2-(3,7,11-Trimethyl-dodecanyl)furan was obtained.

In view of the many possible embodiments to which the principles of the present disclosure may be applied, it should be recognized that the illustrated embodiments are only preferred examples and should not be taken as limiting the scope of the disclosure. Rather, the scope is defined by the following claims. We therefore claim as our invention all that comes within the scope and spirit of these claims.

We claim:

1. A method, comprising reacting a first feedstock comprising a furan compound with a second feedstock comprising a coupling partner selected from prenol, farnesol, geraniol, cinnamyl alcohol, phytol, myrcene, or any combination thereof in the presence of a heterogeneous catalyst to provide a substituted furan have a structure according to Formula I

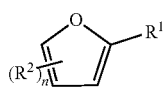

Formula I wherein $R^1$ is an aliphatic group or an aliphatic-aromatic group provided by the coupling partner; and
when n is 1, then $R^2$ is methyl or is the same as $R^1$, and when n is 0, then $R^2$ is not present.

2. The method of claim 1, wherein the ratio of the first feedstock to the second feedstock ranges from 2:1 to 20:1.

3. The method of claim 1, wherein the ratio of the first feedstock to the second feedstock ranges from 5:1 to 15:1.

4. The method of claim 1, wherein the ratio of the first feedstock to the second feedstock ranges from 5:1 to 10:1.

5. The method of claim 1, wherein n is 0 or wherein n is 1 and $R^2$ is methyl.

6. The method of claim 1, wherein the ratio of the second feedstock to the first feedstock ranges from 2:1 to 5:1.

7. The method of claim 1, wherein n is 1 and $R^2$ is the same as $R^1$.

8. The method of claim 1, wherein the heterogeneous catalyst is present in an amount ranging from greater than 0 wt % to 50 wt % of the second feedstock.

9. The method of claim 1, wherein the heterogeneous catalyst is present in an amount ranging from 10 wt % to 50 wt % of the second feedstock.

10. The method of claim 1, wherein the furan compound is furan, 2-methyl furan, 3-methyl furan, or a combination thereof.

11. The method of claim 1, further comprising converting the substituted furan to a hydrogenated product by exposing the substituted furan to a hydrogenation catalyst comprising palladium on a support material selected from activated carbon or $BaSO_4$ in the presence of $H_2$ gas.

12. A method, comprising:
reacting a first feedstock comprising a furan compound with a second feedstock comprising a coupling partner selected from prenol, farnesol, geraniol, cinnamyl alcohol, phytol, myrcene, or any combination thereof in the presence of a heterogeneous catalyst to provide a substituted furan have a structure according to Formula I

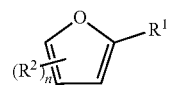

Formula I wherein is an aliphatic group or an aliphatic-aromatic group provided by the coupling partner; and when n is 1, then $R^2$ is methyl or is the same as $R^1$, and when n is 0, then $R^2$ is not present; and exposing the substituted furan to a hydrogenation catalyst comprising palladium on a support material selected from activated carbon or $BaSO_4$ in the presence of $H_2$ gas to provide a selectively hydrogenated substituted furan wherein no olefins of the furan ring are hydrogenated.

13. A method, comprising:
combining a first feedstock, a second feedstock, and a catalyst to provide a feedstock reaction mixture, wherein the first feedstock comprises one of (i) a furan compound or (ii) a coupling partner selected from prenol, farnesol, geraniol, cinnamyl alcohol, phytol, myrcene, or any combination thereof, and wherein the second feedstock comprises the other of (i) the furan compound or (ii) the coupling partner;
allowing the feedstock reaction mixture to mix for a time suitable to provide a substituted furan compound having a structure according to Formula I; and
isolating the substituted furan compound, wherein Formula I is

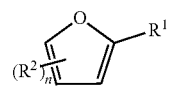

Formula I wherein $R^1$ is an aliphatic group or an aliphatic-aromatic group provided by the coupling partner; and
when n is 1, then $R^2$ is methyl or is the same as $R^1$, and when n is 0, then $R^2$ is not present.

14. The method of claim 13, further comprising exposing the substituted furan to a hydrogenation catalyst comprising palladium on a support material selected from activated carbon or $BaSO_4$ in the presence of $H_2$ gas to provide a selectively hydrogenated substituted furan, wherein no olefins of the furan ring are hydrogenated.

* * * * *